United States Patent
Keane

Patent Number: 5,941,247
Date of Patent: Aug. 24, 1999

[54] SNORE PREVENTION APPARATUS

[76] Inventor: Michael Alexander Keane, 129 N. Cross Creek Rd., #G, Orange, Calif. 92869-5806

[21] Appl. No.: 09/024,687

[22] Filed: Feb. 17, 1998

[51] Int. Cl.⁶ ..................................................... A61F 5/56
[52] U.S. Cl. .......................... 128/848; 128/859; 128/861; 602/902
[58] Field of Search .................... 128/846, 848, 128/859–862; 433/6; 2/2; 602/902

[56] References Cited

U.S. PATENT DOCUMENTS

| | | | |
|---|---|---|---|
| 4,901,737 | 2/1990 | Toone | 128/848 |
| 5,409,017 | 4/1995 | Lowe | 128/859 |
| 5,427,117 | 6/1995 | Thornton | 128/848 |
| 5,570,704 | 11/1996 | Buzzard | 128/848 |
| 5,794,627 | 8/1998 | Frantz | 128/859 |

Primary Examiner—Michael A. Brown
Attorney, Agent, or Firm—Goldstein & Canino

[57] ABSTRACT

A snore prevention apparatus comprising an upper and a lower mouthpiece. The two mouthpieces are conjoined by slideable securing means so that each mouthpiece may move with respect to the other. An air conduit is present between the upper and lower mouthpiece. The apparatus is placed within the user's mouth during sleep periods such that the user's upper teeth engage the upper mouthpiece and his lower teeth engage the lower mouthpiece. The lower mouthpiece is then slideably adjusted forward to maintain the user's lower jaw forward which results in the user's throat opening being enlarged. As the user sleeps and draws breath through his mouth, air travels through the air conduit to the enlarged throat opening, and may then travel down the throat opening with decreased velocity which results in the elimination of resonance which causes snoring.

2 Claims, 4 Drawing Sheets

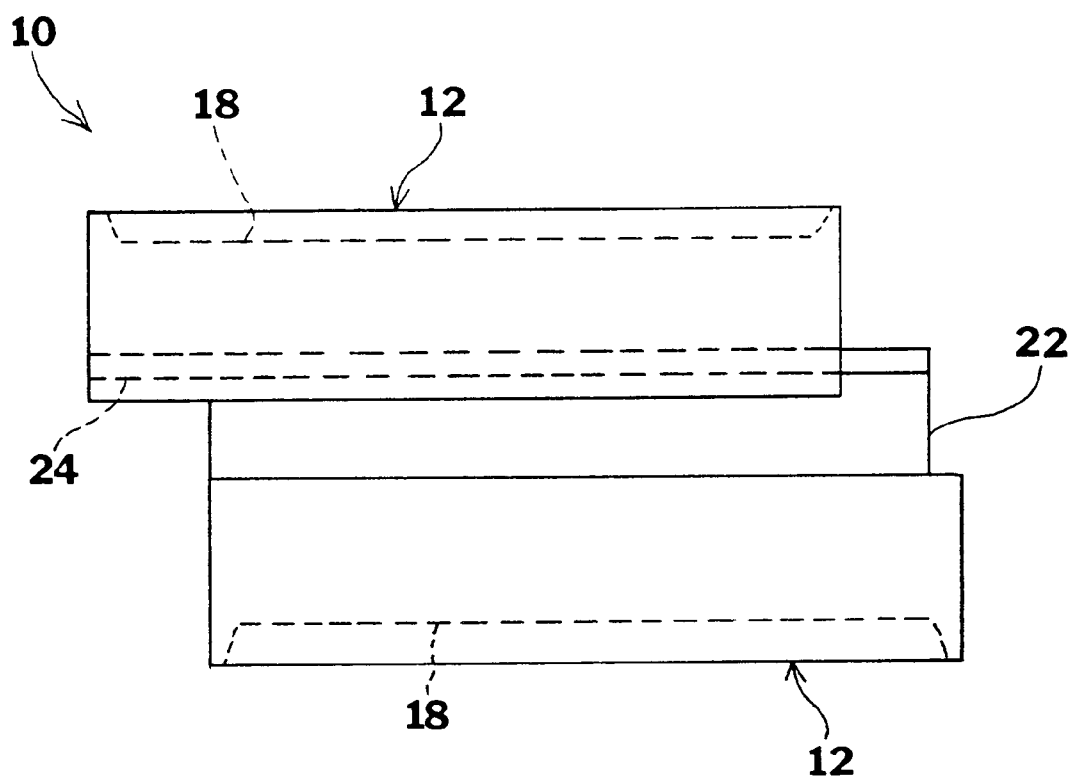

SNORE PREVENTION APPARATUS

FIELD OF THE INVENTION

The invention relates to a snore prevention apparatus. More particularly, the invention relates to an adaptive device which is retained within a user's mouth, and positions the user's lower jaw outward with respect to the user's upper teeth, thus enlarging the user's throat opening during sleeping periods, and preventing said user from snoring.

BACKGROUND OF THE INVENTION

Snoring is an affliction which effects millions of individuals. Often, a snoring individual disturbs others who may be sleeping in proximity thereto. In addition, an individual who tends to snore during resting periods suffers from a lack of uninterrupted sleep in that he or she is awoken numerous times during the evening by the loud sounds of the snoring. As a result, the snoring individual is unable to achieve a healthy, restful complete period of sleep.

Surgical techniques have been available for several years which attempt to permanently correct snoring problems encountered by individuals. However, these surgical procedures are complicated and invasive, sometimes requiring several hours to complete. In addition, numerous medical drawbacks are inherent in the procedure. As a result, the popularity of prostheses and other apparatus has prevailed over the surgical procedure.

Numerous devices are found in the prior art which attempt to alleviate or eliminate this snoring problem without invasive surgery. Most of these devices, however, are bulky and cumbersome, providing great discomfort to the user. For instance, several apparatus found in the prior art comprise devices which are to be installed into the mouth of the user to extend the user's lower jaw forward of his upper teeth in an attempt to enlarge the user's throat opening, thus causing his air passages to become completely unrestricted and alleviating any potential snoring. However, all of these devices which are present in the prior art require customization by a dentist or oral surgeon, thus resulting in prohibitive prices.

These devices which require customization by a dentist or oral surgeon are normally rigidly fixed in place according to the configuration of the user's mouth in a manner which causes the user's lower jaw to extend outward with respect to the upper teeth, as mentioned above. As a result, the fixed device may not be adjusted for comfort at a later time by the user without a return visit to the initial dentists or surgeon who set the device. Accordingly, discomfort and ineffectiveness may ensue until the user is able to return to the dentist or surgeon for re-adjustment.

Accordingly, a need has arisen for a snore-reducing device which may be adjustably configured to be retained comfortably within the mouth of the user to eliminate snoring while the user sleeps.

While these units may be suitable for the particular purpose employed, or for general use, they would not be as suitable for the purposes of the present invention as disclosed hereafter.

SUMMARY OF THE INVENTION

The present invention relates to an adaptive device which is retained within a user's mouth, and positions the user's lower jaw outward with respect to the user's upper teeth, thus enlarging the user's throat opening during sleeping periods, and preventing said user from snoring.

In accordance with the invention, there is provided a snore prevention apparatus for use in the prevention of snoring which overcomes the drawbacks inherent in the above-discussed prior art devices.

Further in accordance with the invention, there is provided a snore prevention apparatus which is adjustable by the user so that said apparatus may be comfortably retained within the user's mouth.

Further in accordance with the invention, there is provided a snore prevention apparatus which maintains a forward position of the users lower jaw with respect to the user's upper teeth so that the user's throat opening is unrestricted and snoring is prevented.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 4 is a side view of the instant invention.

DETAILED DESCRIPTION OF THE PREFERRED EMBODIMENTS

Figure 1:
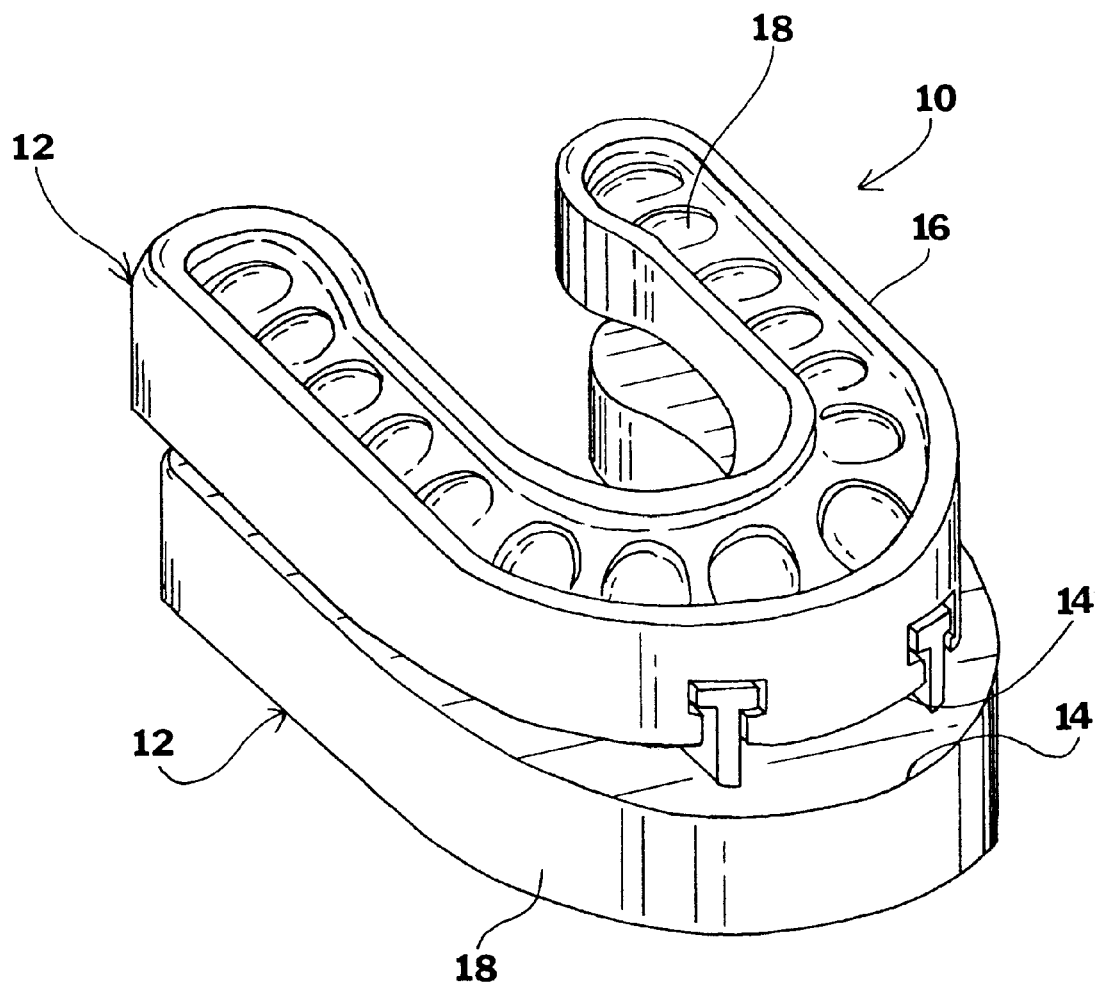
FIG. 1 is a diagrammatic perspective view of the snore prevention apparatus of the instant invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of a snore prevention apparatus 10 as seen in FIG. 1. The words "proximal end" and "distal end" refer, respectively, to ends of an object nearer to and further from the operator of the object when the object is used in a normal fashion or as is described in the specification.

The snore prevention apparatus 10 as seen in FIG. 1 is configured and intended to eliminate or alleviate loud snoring by maintaining a forward posture of a user's lower jaw with respect to the user's upper set of teeth. By biasing said lower jaw in such a fashion, air conduits which lead from the user's mouth to his respiratory system are increased in volume, thus decreasing the velocity of air which passes therethrough and eliminating any resonance which causes snoring.

As seen in FIG. 1, the snore prevention apparatus 10 comprises an upper U-shaped mouthpiece 12 and opposed lower U-shaped mouthpiece 12'. It is contemplated in the preferred embodiment that both mouthpieces be comprised of a non-irritative thermoplastic material. Each mouthpiece 12 and 12' further has a base surface 14 which is bounded on its outer edge perimeter by an upstanding vertical wall 16. The base surface 14 and upstanding vertical wall 16 of each mouthpiece 12 and 12' defines a cavity 18 which is sized to accept a set of human teeth therein. The upper mouthpiece 12 and lower mouthpiece 12' are secured together such that their base surfaces 14 face each other, with the cavities 18 positioned outward, away from the geometric center of the apparatus. Both the upper mouthpiece 12 and lower mouthpiece 12' are essentially identical in size and shape (each conforming to the arch shape of a human set of teeth) since each must accept either an upper or lower set of human teeth which are typically equivalent in size and shape.

Figure 2:
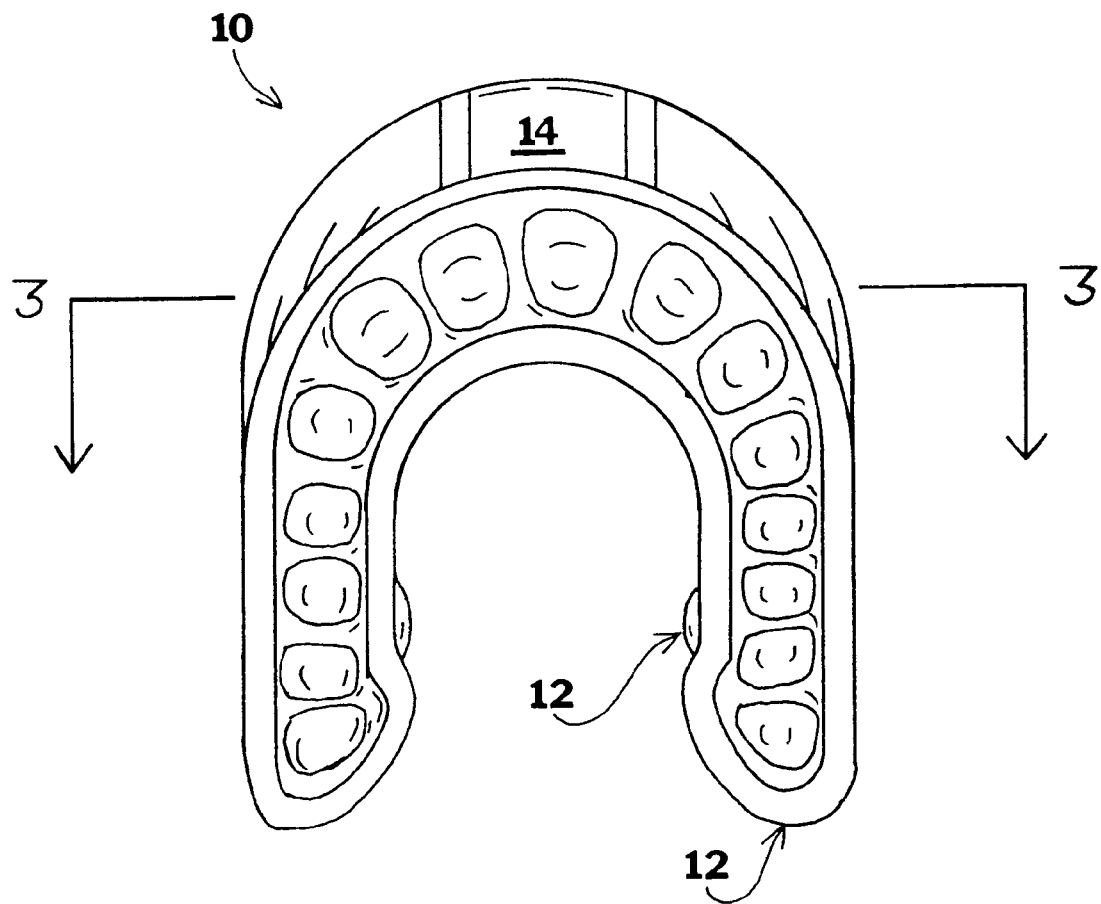
FIG. 2 is a bottom plan view of the snore prevention apparatus of the instant invention.

As mentioned above, the upper mouthpiece 12 and lower mouthpiece 12' are secured together such that their base surfaces 14 face each other, with the cavities 18 positioned outward. An air conduit 20 is also intentionally left between said base surfaces 14 so that air may travel therebetween, as will be discussed in more detail below. Slideable securing means are used to fasten the upper mouth piece 12 to the lower mouth piece 12' so that the two can shift in position with respect to each other. In FIG. 2 and FIG. 4, for example the bottom mouthpiece 12 is shown shifted forward of the top mouthpiece 12'.

Figure 3:
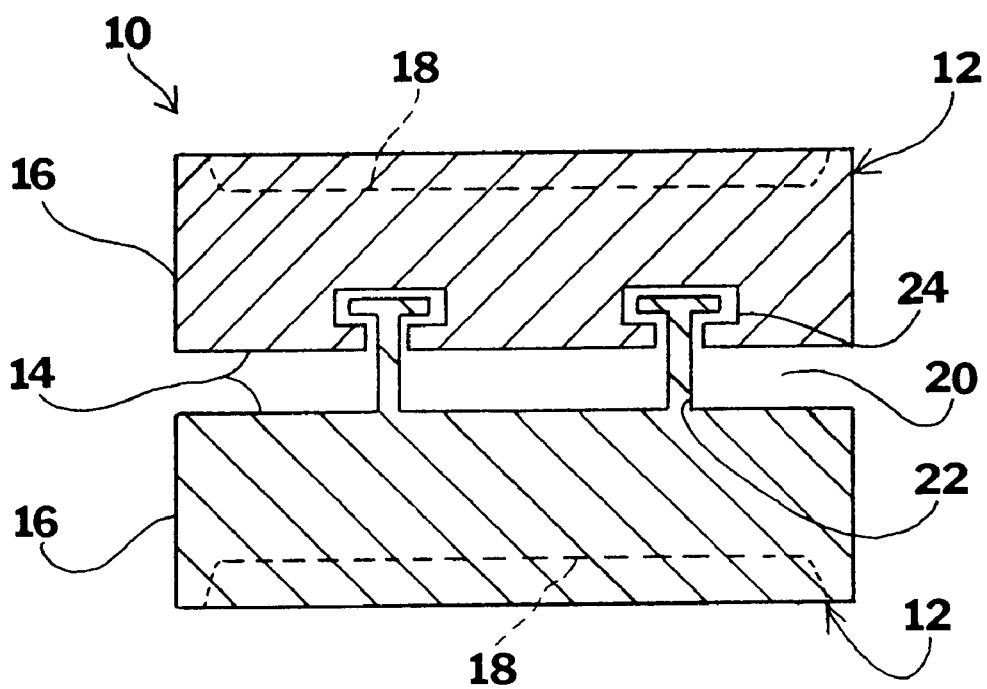
FIG. 3 is a cross sectional view of the instant invention taken on line 3—3 of FIG. 2.

As mentioned earlier, snoring may be prevented by shifting the lower jaw forward with respect to the upper teeth. The instant invention accomplishes this by inserting it into the mouth of a user such that the cavity 18 of the upper mouth piece 12 accepts the user's upper teeth, and the cavity 18 of the lower mouth piece 12' accepts the user's lower teeth. The lower mouth piece 12' is then shifted and held in a forward position, thus holding the user's lower jaw forward as he sleeps, preventing snoring. In FIG. 3, a cross section of the snore prevention apparatus 10 is shown. The slideable securing means are shown thereat, and comprise one or more T-shaped ridges 22 which are integral with and extend upward from the lower mouth piece 12', and are accepted and retained by a plurality of corresponding T-shaped channels 24 which extend through the base surface 14 of the upper mouth piece 12 and are configured to retain said T-shaped ridges while allowing them to slide back and forth within the channel 24.

In the preferred embodiment of the invention, the T-shaped ridges 22 are disposed upon the outer edges of the lower mouthpiece 12' so as to provide the largest air gap 20 therebetween. It is further contemplated that only one T-shaped ridge 22 and corresponding channel 24 may be employed, or any other suitable means which permit the mouthpieces to be secured together yet slide with respect to each other. It is imperative, however, that the air conduit 20 be present between the upper mouthpiece 12 and lower mouthpiece 12' so that when the apparatus is clasped within the mouth of the user with the lower mouthpiece 12' and hence the user's jaw positioned forward, air may pass unrestricted through said air gap 20 to the user's throat opening which is enlarged due to the forward position of the jaw. Since the user's throat opening is enlarged, air may pass through without the typical resonance which results in snoring.

What is claimed is:

1. A snore prevention apparatus to be worn in the mouth of a user while the user sleeps, comprising:

a) an upper mouth piece, substantially U-shaped having a base surface which is bounded by an upstanding vertical wall around its perimeter, the base surface and upstanding vertical wall defining a cavity which is sized to accept a set of upper teeth;

b) a lower mouth piece, substantially U-shaped having a base surface which is bounded by an upstanding vertical wall around its perimeter, the base surface and upstanding vertical wall defining a cavity which is sized to accept a set of lower teeth;

c) slideable securing means which connect the upper mouth piece to the lower mouth piece, such that the base surfaces of the mouth pieces face each other and the open cavities face outward, the slideable securing means permitting the lower mouth piece to be slideably and adjustably positioned forward of the upper mouth piece, said securing means comprising at least one T-shaped ridge which extends from the base surface of one of the mouth pieces towards the base surface of the opposite mouth piece, the opposite mouth piece having at least one corresponding T-shaped channel extending through the surface base thereof which accepts and secures the T-shaped ridge and allows it to adjustably slide forward and rearward therein, thus allowing the lower mouthpiece to be adjusted with respect to the upper mouthpiece; and d) an air conduit between the base surfaces of the opposed upper mouthpiece and lower mouthpiece, whereby the apparatus is inserted into the user's mouth such that user's upper teeth engage the cavity of the upper mouthpiece and the user's lower teeth engage the cavity of the lower mouthpiece, the lower mouthpiece then adjusted forward to maintain a forward posture of the user's lower jaw, thus enlarging the user's throat opening so that air may pass through the air conduit and down the enlarged throat opening at a decreased velocity such that resonance which causes snoring during sleep is eliminated.

2. The snore prevention apparatus of claim 1, wherein the upper and lower mouthpieces are comprised of a non-irritative thermoplastic material.

* * * * *